United States Patent
Erkens et al.

(10) Patent No.: US 10,945,930 B2
(45) Date of Patent: *Mar. 16, 2021

(54) THICKENER IN A PERCARBONATE-CONTAINING BLEACHING AGENT CONTAINED IN A MULTI-LAYER SACHET

(71) Applicant: Henkel AG & Co. KGaA, Duesseldorf (DE)

(72) Inventors: Udo Erkens, Willich (DE); Torsten Lechner, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/697,598

(22) Filed: Nov. 27, 2019

(65) Prior Publication Data
US 2020/0206102 A1 Jul. 2, 2020

(30) Foreign Application Priority Data

Dec. 28, 2018 (DE) .................... 10 2018 133 663.2

(51) Int. Cl.
| | | |
|---|---|---|
| *A61Q 5/00* | (2006.01) | |
| *A61K 8/22* | (2006.01) | |
| *A61K 8/23* | (2006.01) | |
| *A61K 8/02* | (2006.01) | |
| *A61K 8/73* | (2006.01) | |
| *A61K 8/81* | (2006.01) | |
| *A61K 8/26* | (2006.01) | |
| *A61Q 5/08* | (2006.01) | |
| *A61K 8/85* | (2006.01) | |

(52) U.S. Cl.
CPC .............. *A61K 8/22* (2013.01); *A61K 8/0216* (2013.01); *A61K 8/23* (2013.01); *A61K 8/26* (2013.01); *A61K 8/731* (2013.01); *A61K 8/8111* (2013.01); *A61K 8/85* (2013.01); *A61Q 5/08* (2013.01); *A61K 2800/48* (2013.01)

(58) Field of Classification Search
CPC ... A61Q 5/08; A61K 8/22; A61K 8/19; A61K 8/23; A61K 8/46; A61K 8/731; A61K 8/73; A61K 8/26; A61K 2800/48; A61K 8/85; A45D 2007/001
USPC .......................................................... 424/62
See application file for complete search history.

(56) References Cited

U.S. PATENT DOCUMENTS

| | | | |
|---|---|---|---|
| 2011/0232669 A1* | 9/2011 | Suenger ................... | A61K 8/44 132/208 |
| 2013/0042883 A1 | 2/2013 | DeGeorge et al. | |
| 2017/0007856 A1 | 1/2017 | Aubert et al. | |

FOREIGN PATENT DOCUMENTS

| | | |
|---|---|---|
| EP | 1036813 A1 | 9/2000 |
| GB | 2570395 A | 7/2019 |
| WO | 2014029657 A2 | 2/2014 |

OTHER PUBLICATIONS

Mintel: "Nouvelle New Generation DecoFlash Bleaching Powder", record ID 2864949, Dec. 2014.
Mintel: "Effervescent Nail Cleaner", record ID 10094957, Oct. 2001.

* cited by examiner

*Primary Examiner* — Eisa B Elhilo
(74) *Attorney, Agent, or Firm* — Lorenz & Kopf, LLP

(57) ABSTRACT

The present disclosure relates to a cosmetic agent for bleaching human hair, comprising (i) a package comprising at least one multi-layer film, which comprises at least one metal-containing layer as a barrier layer, and (ii) a bleaching agent composition, which is contained in the package, wherein the bleaching agent composition contains at least one percarbonate, at least one inorganic salt of a peroxysulfuric acid, and at least one thickener. The present disclosure also relates to a method for bleaching human hair.

19 Claims, No Drawings

THICKENER IN A PERCARBONATE-CONTAINING BLEACHING AGENT CONTAINED IN A MULTI-LAYER SACHET

CROSS-REFERENCE TO RELATED APPLICATION

This application claims priority to German Patent Application No. 10 2018 133 663.2, filed Dec. 28, 2018, which is incorporated herein by reference in its entirety.

TECHNICAL FIELD

The present disclosure relates to a cosmetic product for bleaching human hair, comprising (i) a package comprising at least one multi-layer film, which comprises at least one metal-containing layer as a barrier layer, and (ii) a bleaching agent composition, which is contained in the package, wherein the bleaching agent composition contains at least one percarbonate, at least one inorganic salt of a peroxysulfuric acid, and at least one thickener. The present disclosure also relates to a method for bleaching human hair.

BACKGROUND

To lighten or bleach their hair or generally to make an oxidative colour change has always been the desire of many consumers, because a blond hair colour is considered to be attractive and a worthwhile objective from a fashion point of view. For this purpose, various bleaching agents with different bleaching strengths are available on the market. The oxidizing agents contained in these products are able to lighten the hair fibres by the oxidative destruction of the pigment melanin naturally present in the hair and/or of artificial dyes. For a moderate bleaching effect, it is sufficient to use hydrogen peroxide alone as oxidizing agent—possibly together with ammonia or other alkalizing agents. To obtain a stronger bleaching effect, usually a mixture of hydrogen peroxide and peroxy salts, particularly persulfate salts, is used.

These peroxy salts are typically used in the form of a powder, which is mixed with a hydrogen peroxide preparation shortly before it is applied. Use of the combination of hydrogen peroxide and persulfates is associated with various drawbacks. For example, the components hydrogen peroxide and persulfate have to be packaged separately, since they react with one another.

In order to produce the ready-to-use bleaching agent, at least two separately packaged components (the persulfate powder and the hydrogen peroxide solution) thus have to be mixed with one another. The sustainability-minded user is also paying closer attention to the ecological aspects of a given product. One objective in this context is also to reduce the amount of packaging material used. Products which are used in the most concentrated form possible, which include only one component, and which only need to be mixed with water to produce the application mixture optimally offer a decisive advantage with regard to saving packaging material.

A package of this kind can be produced for example by gluing or hot pressing two plastic films arranged one on top of the other, wherein the gluing is provided at all edges of the films. The interior of the package (i.e. of the plastic bag) produced by the gluing may then be filled with the desired cosmetic preparation. The package may be opened by tearing open or cutting open the plastic bag.

The filling of oxidizing agent preparations into packages of this kind, however, is associated with problems caused by the reactivity of the oxidizing agent. Oxidizing agents are highly reactive, usually liquid or pasty substances, which—depending on the storage conditions and the presence of any contaminations that have a destructive effect—break down in small amounts and thus form oxygen (i.e. gas).

The developer bottles known from the prior art are generally only filled to at most half, usually merely to a third of their interior volume with the oxidizing agent composition. Developer bottles are generally made of polyethylene. Since polyethylene is permeable both to water vapour and to gases; there is no, or only very low overpressure in the developer bottle. In addition, developer bottles are usually provided with stable, thick walls and a stable screw cap, and therefore the diffusion of the water vapour or the gases is reduced by the thickness of the walls and a pressure increase occurring to a small extent within the bottle has no negative effects.

The packages are consequently usually bulky, to the detriment of the sustainability in respect of environmental protection and conservation of resources. It would be advantageous if a solid were used as oxidizing agent instead of liquid hydrogen peroxide. Then, the bleaching agent components could be provided also in a container, since the reaction of the components would only require a step of mixing with water.

Persulfates and percarbonates are known as solid oxidizing agents for bleaching agents. They are used as salts. The use of salts, however, is in turn disadvantageous for the setting of the viscosity of the ready-to-use cosmetic composition. Specifically, polyelectrolytes, for example xanthan, which lose their effect of increasing viscosity as the salt content increases, are often used as thickener. If the ready-to-use cosmetic product has an excessively low viscosity, it can only be applied disadvantageously and is thus more difficult to handle.

BRIEF SUMMARY

Cosmetic products and methods for bleaching human hair with the same are provided. In an exemplary embodiment, the cosmetic product includes a package and a bleaching agent composition contained within the package. The package has at least one multi-layer film with at least one metal-containing layer as a barrier layer. The bleaching agent composition includes at least one percarbonate, at least one inorganic salt of a peroxysulfuric acid, and at least one thickener.

A method for bleaching human hair is provided in another embodiment. The method includes introducing a bleaching agent composition into an amount of water, homogenizing the bleaching agent composition and the water, and applying the homogenized mixture to the human hair. The bleaching agent composition includes at least one percarbonate, at least one inorganic salt of a peroxysulfuric acid, and at least one thickener.

A cosmetic product is provided in another embodiment. The cosmetic product includes a package and bleaching agent composition contained within the package. The package includes at least one multi-layer film, wherein the multi-layer film comprises a first polymer layer (P1), a second polymer layer (P2) and a barrier layer (BS). The first polymer layer (P1) includes polyethylene terephthalate and has a layer thickness of from about 10 to about 14 µm, and the second polymer layer (P2) includes polyethylene and has a layer thickness of from about 70 to about 80 µm. The barrier layer (BS) includes aluminium and has a layer thickness of from about 8 to about 12 μm. The bleaching agent composition includes a percarbonate, an inorganic salt of a peroxysulfuric acid, and a thickener. The percarbonate is sodium percarbonate and is present in the bleaching agent composition at from about 6 to about 12 wt %. The inorganic salt of a peroxysulfuric acid is selected from mixtures of potassium peroxydisulfate and ammonium peroxydisulfate, and mixtures of sodium peroxydisulfate and ammonium peroxydisulfate, and is present in the bleaching agent composition at from about 10 to about 70 wt %. The thickener includes a mixture of a cellulose gum, a hydroxyethyl cellulose and a xanthan gum, wherein the quantity of cellulose gum is from about 0.2 to about 5 wt %, the quantity of xanthan gum is from 0.1 to 5 wt %, and the quantity of hydroxyethyl cellulose is from 0.2 to 5 wt %, where all wt % values are in relation to a total weight of the bleaching agent composition.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present application thus lies in providing a cosmetic bleaching composition which can be packaged securely and in a space-saving fashion in less packaging material, without having to accept any disadvantages in respect of the handling, in particular in respect of the viscosity of the ready-to-use cosmetic product. Furthermore, the cosmetic bleaching composition should be packaged so that the mechanical strength of the package is sufficient to enable secure and space-saving storage, wherein simple accessibility of the ingredients should be ensured.

The object forming the basis of the present disclosure is achieved by the subject matter of claim 1. A first subject of the present disclosure is therefore a cosmetic product for bleaching keratin fibres, in particular human hair, comprising
(i) a package comprising at least one multi-layer film, which comprises at least one metal-containing layer as a barrier layer, and
(ii) a bleaching agent composition, which is contained in the package, exemplified in that the bleaching agent composition contains
at least one percarbonate,
at least one inorganic salt of a peroxysulfuric acid, and
at least one thickener.

Keratinous fibres, keratin-containing fibres or keratin fibres are understood to mean furs, wool, feathers and, in particular, human hair. Although the products as contemplated herein are primarily suitable for lightening keratin fibres, they can in principle be used also in other fields.

The product as contemplated herein is a product for oxidatively changing the colour of keratin fibres, i.e. a product which is applied to the human head in order to attain an oxidative lightening or tinting of the hair. In this context, "tinting" is understood to mean colouring in which the colour result is lighter than the starting hair colour.

The cosmetic product as contemplated herein comprises, as a first constituent, a package (VP) which comprises at least one multi-layer film (F). This film contains at least one first polymer layer (P1), at least one second polymer layer (P2) and at least one barrier layer (BS). This multi-layer film constitutes the wall or the outer sleeve of the package. As described before, a package of this kind is usually produced by gluing, pressing or welding two film pieces arranged one above the other (wherein the package (VP) is filled at the same time with the bleaching agent composition), i.e. a package of this kind is sealed at all edges. This package may be opened for example by being torn open or cut open.

The thickness of the multi-layer film (F) should be such that a sufficient mechanical stability is provided, but at the same time the film (F)—and thus the package (VP) produced from the film—is flexible enough that the entire bleaching composition can be removed from the opened package (VP) by compressing the package or by being pressed out. These requirements are satisfied in particular if the film (F) has a certain overall thickness. Preferred embodiments of the present disclosure are therefore exemplified in that the at least one multi-layer film has an overall thickness of from about 21 μm to about 2.0 mm, preferably from about 30 μm to about 1.0 mm, preferably from about 50 μm to about 500 μm, in particular from about 60 μm to about 200 μm. The overall thickness of the film (F) is understood in the sense of the present disclosure to mean the sum of the thicknesses of all individual layers from which the film (F) is made.

The term "package" is also understood as contemplated herein to mean a package which is provided in accordance with the present disclosure in the form of a sachet. In a particular embodiment described below, the package may also be a double sachet. A sachet (pouch) is a small package in pocket or bag form, which is often used in the packaging of cosmetics. The holding capacity of the package, in particular the sachet, can be for example from about 5 to about 1000 ml, preferably from about 10 to about 200 ml, and particularly preferably from about 20 to about 50 ml.

A double sachet is a sachet that has two separate chambers. The portioning itself in a double sachet is more space-saving than the portioning of hydrogen peroxide in a plastic bag. By using a double sachet, the handling of the bleaching agent composition is simplified significantly. The percarbonate may be contained in one chamber, and the inorganic salt of the peroxysulfuric acid may be contained in the other chamber. Providing the cosmetic product in the form of a double sachet offers the advantage of space-saving storage and simpler handling. The sachet or double sachet can be easily torn open and blended with water so as to achieve a ready-to-use product.

Percarbonates and salts of peroxysulfuric acid which are suitable for bleaching agents are generally solid substances. The percarbonate and the salt of the peroxysulfuric acid which are used in the cosmetic product as contemplated herein are preferably solids, in particular powdered solids. Since the bleaching agent composition is contained in the package, it is ensured that the bleaching agent composition can be easily handled and reliably dosed. The used percarbonate and the used salt of the peroxysulfuric acid do not form dust, since they are contained in the package within the closed chamber. The package in the case of the cosmetic product as contemplated herein thus forms a closed chamber. This can be ensured by sealing or gluing the chamber once the bleaching agent composition has been introduced into the package.

The cosmetic product as contemplated herein is used for oxidatively lightening human hair. The term "oxidative lightening" is understood to refer also to agents for lightening keratin fibres which contain the percarbonate and the salt of the peroxysulfuric acid. If the intended result is simple bleaching or lightening, the cosmetic products contain no other dyes. However, the intention may be to impart tinting to the keratin fibres in addition to the bleaching/lightening effect. For the purpose of tinting, the cosmetic products as contemplated herein may also contain additional colouring components such as substantive dyes and/or precursor products of oxidation dyes. However, the preferred purpose of the cosmetic products is bleaching or lightening, and therefore the cosmetic products preferably contain either no dyes or only very small quantities thereof, suitable only for slight tinting.

As a first component, the bleaching agent composition contains at least one percarbonate. This is used as contemplated herein as a replacement for hydrogen peroxide. The mixing of the components of the bleaching agent composition comprising the percarbonate creates hydrogen peroxide for the bleaching of hair.

In accordance with a preferred embodiment of the present disclosure, the cosmetic product contains a bleaching composition in which the at least one percarbonate is an alkaline or alkaline earth metal or ammonium salt of a percarbonate, in particular sodium percarbonate. The at least one percarbonate, in particular sodium percarbonate, is preferably contained in the bleaching agent composition in a total quantity of from about 2 to about 14 wt %, preferably from about 6 to about 12 wt %, in relation to the total weight of the bleaching agent composition.

A percarbonate shall be understood preferably to mean an $H_2O_2$ adduct. In the sense of the present disclosure, sodium percarbonate is understood to mean the adduct (or the complex) of sodium carbonate and hydrogen peroxide with the composition 2 $Na_2CO_3 \cdot 3\ H_2O_2$. Sodium percarbonate forms a white, water-soluble powder, which breaks down upon contact with water into sodium carbonate and hydrogen peroxide. The sodium percarbonate as contemplated herein (2 $Na_2CO_3 \cdot 3H_2O_2$) has a molar mass of about 314.02 g/mol and has the CAS number 15630-89-4.

Sodium percarbonate is available commercially in various degrees of purity from a number of providers. For example, the company Evonik Degussa offers a sodium percarbonate with a purity of about 98.8 wt %. All the aforementioned quantity specifications are indicated in relation to 100% sodium percarbonate. If sodium percarbonate with lower degrees of purity is used, the quantities for use must be recalculated correspondingly.

In the sense of the present disclosure, potassium percarbonate is understood to mean the adduct (or the complex) of potassium carbonate and hydrogen peroxide with the composition 2 $K_2CO_3 \cdot 3H_2O_2$.

The use of sodium percarbonate has proven to be particularly well suited for solving the problem addressed by the present disclosure.

It was found that hair damage could be reduced when smaller quantities of percarbonates than is conventionally the case were used in the cosmetic products. The research that resulted in this present disclosure showed that a further increase in the quantity of percarbonate above about 14 wt % is more damaging to the hair but does not further enhance the lightening effect. In this context, it was found to be preferable to use the percarbonate in the preferred quantity ranges. The best lightening effect with the comparatively least hair damage was obtained when the cosmetic products contained the percarbonates (particularly sodium percarbonate) in a total quantity from about 6 to about 12 wt %.

All the aforementioned specifications in wt % in the context of the present disclosure are indicated in relation to the total weight of the bleaching agent composition or the total weight of components in the various chambers (in the case of double-chamber sachets), depending on the indication. If a mixture of sodium percarbonate and potassium percarbonate is used, of course the specifications in wt % relate to the sum of the percentages by weight. Of course, the same applies for the salts of peroxysulfuric acid.

As a second constituent of the bleaching agent composition essential to the present disclosure, the cosmetic product contains in the bleaching agent composition at least one salt of peroxysulfuric acid. Peroxysulfuric acids are understood to be peroxydisulfuric acid and peroxymonosulfuric acid (Caro's acid).

In accordance with a preferred embodiment of the present disclosure the at least one inorganic salt of a peroxysulfuric acid is selected from the group including sodium peroxydisulfate, potassium peroxydisulfate, ammonium peroxydisulfate, sodium peroxymonosulfate, potassium peroxymonosulfate and ammonium peroxymonosulfate. Or, the inorganic salt of a peroxysulfuric acid comprises mixtures of the stated inorganic salts of a peroxysulfuric acid, preferably mixtures of potassium peroxydisulfate and ammonium peroxydisulfate or mixtures of sodium peroxydisulfate and ammonium peroxydisulfate. In accordance with a preferred embodiment of the present disclosure the total quantity of inorganic salt of a peroxysulfuric acid is from about 10 to about 70 wt %, more preferably from about 20 to about 50 wt %, even more preferably from about 25 to about 45 wt %, most preferably from about 30 to about 40 wt %, in each case in relation to the total weight of the bleaching agent.

In accordance with a particularly preferred embodiment of the present disclosure the inorganic salt of a peroxysulfuric acid is a mixture comprising from about 5 to about 40 wt %, preferably from about 10 to about 35 wt %, more preferably from about 15 to about 30 wt % potassium peroxydisulfate, from about 5 to about 20 wt %, preferably from about 8 to about 18 wt %, more preferably from about 10 to about 15 wt % ammonium peroxydisulfate, and from about 0 to about 10 wt %, preferably from about 1 to about 9 wt %, more preferably from about 2 to about 6 wt % sodium peroxydisulfate, in each case in relation to the total weight of the bleaching agent.

Ammonium persulfate is alternatively also referred to as ammonium peroxydisulfate and has the empirical formula $(NH_4)_2S_2O_8$. Ammonium persulfate has the CAS number 7727-54-0. Potassium persulfate is alternatively also referred to as potassium peroxydisulfate and has the empirical formula $K_2S_2O_8$. Potassium persulfate has the CAS number 7727-21-1. Sodium persulfate is alternatively also referred to as sodium peroxydisulfate and has the empirical formula $Na_2S_2O_8$. Sodium persulfate has the CAS number 7775-27-1.

The salts of peroxysulfuric acid are preferably used in specific total quantities in the cosmetic product as contemplated herein so as to both optimise the lightening effect and also minimise hair damage.

The bleaching agent composition contains as a third essential ingredient at least one thickener.

In addition, the term "thickener" within the scope of the present disclosure is understood to mean compounds which can bind liquids, in particular water, and which increase the viscosity of these liquids. Thickeners within the scope of the present disclosure also include gel formers, which are able to thicken liquids so as to form compositions having a gel-like consistency, or so as to form gels. The terms "thickening agent" and "thickener" are used synonymously within the scope of the present disclosure. Gel-like cosmetic products or gels are understood as contemplated herein to mean dimensionally stable, easily deformable, disperse systems formed from at least two components: the gel former (usually a solid, colloid-split substance with long or heavily branched compounds) and a liquid (usually water) as dispersant. The gel former in the liquid forms a spatial network, wherein the individual gel-forming compounds adhere to one another by primary and/or secondary valences at different spatial points among one another.

In accordance with a preferred embodiment of the present disclosure the at least one thickener is a polysaccharide, preferably a mixture of at least two different polysaccharides, more preferably a mixture of an at least partially ionic polysaccharide and a substantially non-ionic polysaccharide.

As described above, it has proven to be a particular challenge to formulate a cosmetic product for lightening hair which uses solid substances as oxidizing agent and no liquid hydrogen peroxide as a component and which at the same time comprises a thickener which sets the viscosity of the ready-to-use cosmetic composition to an advantageous value. The problem lies in the fact that thickeners which are polyelectrolytes lose their viscosity-increasing properties as the salt content increases. It has proven to be particularly advantageous if a mixture of two different polysaccharides is used as thickener.

In accordance with a preferred embodiment of the present disclosure the at least one thickener is contained in the bleaching agent composition in a total quantity of from about 0.5 to about 15 wt %, preferably from about 1 to about 10 wt %, more preferably from about 4 to about 8 wt %, in relation to the total weight of the bleaching agent composition.

Rigorous tests have surprisingly revealed that a mixture of three thickeners is particularly well suited for achieving the advantageous effect in respect of viscosity. A particularly preferred embodiment of the present disclosure is therefore a cosmetic product in which the at least one thickener is a mixture of a cellulose gum, a hydroxyethyl cellulose and a xanthan gum, wherein preferably the quantity of cellulose gum is from about 0.2 to about 5 wt %, preferably from about 0.5 to about 3 wt %, the quantity of xanthan gum is from about 0.1 to about 5 wt %, preferably from about 0.5 to about 2 wt %, and/or the quantity of hydroxyethyl cellulose is from about 0.2 to about 5 wt %, preferably from about 0.5 to about 4 wt %, in each case in relation to the total weight of bleaching agent composition.

Within the scope of the present disclosure the use of xanthans which have a mean particle diameter D50 of from about 140 to about 200 μm and a viscosity (0.3 wt % solution in 0.3% KCl) of from about 250 to about 800 mPas (measured with a Brookfield viscometer at 3 rpm) have proven to be particularly advantageous. Xanthans of this kind are commercially available from the company CP Kelco, for example under the trade name Keltrol CG-SFT.

As contemplated herein the term "xanthans" means naturally occurring polysaccharides which can be obtained with the aid of bacteria of the *Xanthomonas* genus from sugar-containing substrates. The xanthan used as contemplated herein preferably contains d-glucose, d-mannose, d-glucuronic acid, acetate and pyruvate in a molar ratio of 28:30:20:17:5.1-6.3, wherein the main chain include β-1,4-linked glucose units (also referred to as the cellulose chain). The xanthans used with particular preference within the scope of the present disclosure have the CAS number 11138-66-2 and the following structural formula

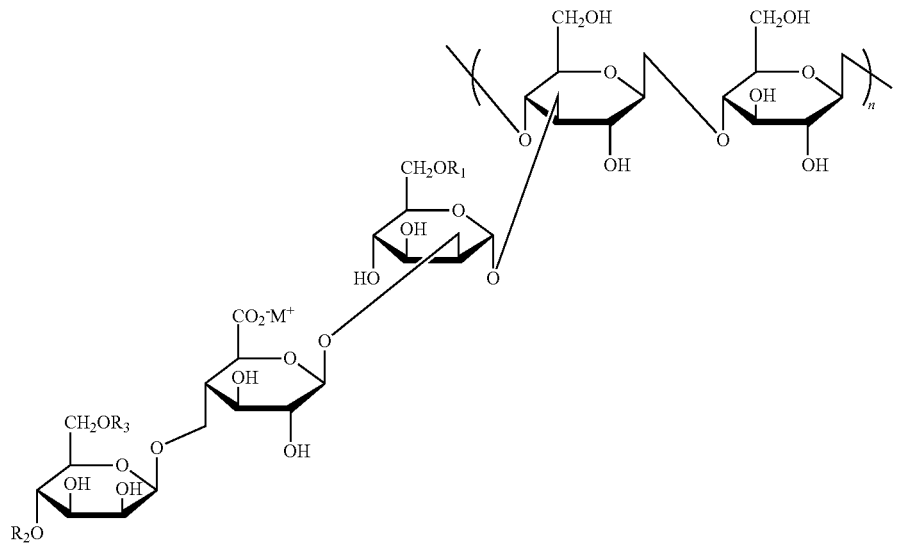

$M^+ = Na, K, 1/2\ Ca$

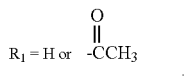

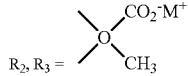

$R_2, R_3 = H$ or

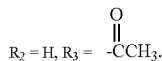

Xanthan constitutes a polyelectrolyte due to its structure. The further special thickening agents Cellulose Gum (carboxymethyl cellulose) and hydroxyethyl cellulose are commercially available under the product names Cekol 5000 and Tylose H 100.000 YP2. The hydroxyethyl cellulose is a cellulose ether and comprises substantially no free acid groups.

The research that resulted in this present disclosure showed that, by use of the aforementioned specific thickener, in particular the preferred mixtures, the bleaching agent composition can be formulated and stored in the special package (VP) which, without this packaging—which has a barrier layer with a penetration barrier effect for gases and water vapour—results in swelling or bursting. These cosmetic products can also be handled particularly advantageously.

In accordance with a preferred embodiment of the present disclosure the cosmetic product is free from hydrogen peroxide. This means that the cosmetic product is substantially free from hydrogen peroxide, in particular that no hydrogen peroxide is added to the bleaching agent composition during the packaging process. Of course, traces of water may be contained in the cosmetic product, and therefore hydrogen peroxide is created during reaction with the percarbonate. This, however, should lead only to a small amount of free hydrogen peroxide. Hydrogen peroxide may of course also be provided formally in the empirical formula of the solid oxidizing agent, in the crystal structure of the carbonate. It is therefore also not present in the form of free hydrogen peroxide.

In accordance with a preferred embodiment of the present disclosure a cosmetic product is provided in which the package is a single-chamber sachet in which the components of the bleaching agent composition are provided. In this embodiment the product is one that is particularly easily handled. It has surprisingly been found that the combination of the multi-layer film, the percarbonate and the inorganic salt of a peroxysulfuric acid together with the thickener fully solves the problem forming the basis of the present disclosure.

Alternatively the package may be a two-chamber bag in which the percarbonate is contained in a first chamber of the two-chamber bag and the inorganic salt of a peroxysulfuric acid is contained in a second chamber of the two-chamber bag, wherein the multi-layer film (F) preferably has an oxygen transmission rate (OTR) at 23° C. and 0% relative humidity of less than about 0.1 cc/m²/d/bar, and a water vapour permeability at 38° C. and 90% relative humidity of less than about 0.1 g/m²d.

In accordance with a preferred embodiment of the present disclosure, the cosmetic product may be one in which the multi-layer film comprises at least one first polymer layer (P1), at least one second polymer layer (P2) and the barrier layer (BS), wherein the first polymer layer (P1) is formed from polyethylene terephthalate or polyethylene naphthalate, in particular from polyethylene terephthalate; the second polymer layer (P2) is formed from a polyolefin, in particular polyethylene; and/or the metal-containing layer is formed from aluminium; wherein the first polymer layer (P1) preferably has a layer thickness of from about 5 to about 20 μm, preferably from about 8 to about 16, more preferably from about 10 to about 14 μm; the second polymer layer preferably has a layer thickness of from about 50 to about 100 μm, preferably from about 60 to about 90 μm, more preferably from about 70 to about 80 μm; and the metal-containing layer preferably has a layer thickness of from about 3 to about 30 μm, preferably from about 5 to about 15 μm, more preferably from about 8 to about 12 μm.

In accordance with a preferred embodiment of the present disclosure a cosmetic product is provided in which the barrier layer (BS) is arranged between the first polymer layer (P1) and the second polymer layer (P2), and/or wherein the first polymer layer is situated on the side facing away from the bleaching agent composition. What is meant is that the first polymer layer is arranged externally and the second polymer layer is arranged internally, that is to say facing the agent.

In accordance with a preferred embodiment of the present disclosure a cosmetic product is provided, in which the package constitutes a one-chamber sachet in which the percarbonate and the inorganic salt of a peroxysulfuric acid are present; or exemplified in that the package is a two-chamber bag and the percarbonate is contained in a first chamber of the two-chamber bag and the inorganic salt of a peroxysulfuric acid is contained in a second chamber of the two-chamber bag, wherein the multi-layer film (F) preferably has an oxygen transmission rate (OTR) at 23° C. and 0% relative humidity of less than about 0.1 cc/m²/d/bar, and a water vapour permeability at 38° C. and 90% relative humidity of less than about 0.1 g/m²d. In this preferred embodiment the thickener may be contained in the first and/or second chamber.

In accordance with a preferred embodiment of the present disclosure a cosmetic product is provided, in which the two-chamber bag forms a first multi-layer film (F1), which forms the packaging of the first chamber, and a second multi-layer film (F2), which forms the packaging of the second chamber, wherein the oxygen transmission rate (OTR) and the water vapour permeability of the first multi-layer film (F1) are different from the oxygen transmission rate (OTR) and the water vapour permeability of the second multi-layer film (F2); wherein the first multi-layer film (F1)

has an oxygen transmission rate (OTR) at 23° C. and 0% relative humidity of from about 0.1 to about 5 cc/m²/d/bar, preferably of from about 0.2 to about 3.5 cc/m²/d/bar, more preferably of from about 0.5 to about 2.5 cc/m²/d/bar, and a water vapour permeability at 38° C. and 90% relative humidity of from about 0.1 to about 5 g/m²d, preferably from about 0.2 to about 3.5 g/m²d, more preferably from about 0.5 to about 2.5 g/m²d, and the second multi-layer film (F2) has an oxygen transmission rate (OTR) at 23° C. and 0% relative humidity of from about 0.01 to about 0.1 cc/m²/d/bar, preferably of from about 0.02 to about 0.09 cc/m²/d/bar, more preferably of from about 0.05 to about 0.08 cc/m²/d/bar, and a water vapour permeability at 38° C. and 90% relative humidity of from about 0.01 to about 0.1 g/m²d, preferably from about 0.02 to about 0.09 g/m²d, more preferably from about 0.05 to about 0.08 g/m²d.

This preferred embodiment is thus understood to mean that, for the case in which the two-chamber bag is formed from two different films, the second multi-layer film (F2) has an oxygen transmission rate (OTR) and a water vapour permeability which are equal to or less than the oxygen transmission rate (OTR) and the water vapour permeability of the multi-layer film (F) when the package is formed merely from one multi-layer film (F). The advantage of this preferred embodiment lies in the adaptation of oxygen transmission rate (PTR) and water vapour permeability depending on the content. The peroxide-containing composition must be stored differently from the percarbonate composition, in particular under consideration of the oxygen permeability, and the percarbonate composition on account of the pH values must be stored differently from the persulfate composition under consideration of the water vapour permeability. The permeability parameters can be adjusted by the thickness of the barrier layer (BS). A two-chamber bag can be produced in accordance with this preferred embodiment such that the edges of the two chambers are laid one above the other and are glued along their sealing edge seams. Other production methods are also conceivable.

In addition, a multi-layer film (F) within the scope of the present disclosure is understood to mean a thin, planar web that can be rolled up and which is formed of the at least one polymer layer (P1) and the at least one polymer layer (P2). This multi-layer film (F) forms the wall of the package (VP). The polymer layers (P1) and (P2) preferably comprise polymers that are able to form films. Furthermore, the polymer layers (P1) and (P2) are preferably polymer layers different from one another. The package additionally contains a barrier layer (BS) which prevents or reduces the passage of water vapour and other gases, such as oxygen, that is to say prevents or reduces the diffusion of these gases through the wall of the package. As contemplated herein the permeability of the film (F) is set to advantageous values. The film (F) thus provides the package with advantageous barrier properties, in particular in respect of the permeability for water vapour (water vapour transmission rate or WVTR; measured in the unit g/(m²d) or g/(m²24h)) measured in accordance with the method ASTM E 398 at 38° C. ambient temperature and 90% relative humidity, and for oxygen (oxygen transmission rate or OTR; measured in cm³/(m²d bar) or cm³/(m² 24 h)—wherein cm³ is equivalent with cc—at an atmospheric pressure of 1 bar) measured in accordance with the method ASTM D 3985 at 23° C. ambient temperature and 0% relative humidity.

In accordance with a preferred embodiment of the present disclosure the first chamber and the second chamber of the double-chamber sachet are separated from one another at least by a sealing seam, and the two-chamber bag is provided with a perforation which, when severed, opens both chambers of the two-chamber bag When the perforation is severed, an opening is created in each chamber, through which openings the content of the first chamber and the content of the second chamber can escape. The feature that the two chambers of the two-chamber bag should be separated from one another "at least" by a sealing seam, is intended to mean that further features may be implemented between the bags, for example a perforation may be situated along the sealing seam, wherein the separation of the perforation signifies a separation of the two bags of the two-chamber bag. Alternatively, the two chambers may be separated by a film. In that case, the double sachet appears to be a single sachet from the outside, wherein the chambers are separated from one another only by the film or possibly by a double film, wherein the separating film or separating double film is arranged between the two outer films.

The arrangement of the layers (P1), (P2) and (BS) within the multi-layer film (F) may be different. It is furthermore also possible that the film (F) also comprises further layers in addition to the above-mentioned layers. In addition, it is advantageous as contemplated herein if all aforementioned layers are each oriented parallel to the surfaces of the film (F), that is to say all layers have the same orientation.

It is particularly preferred embodiment as contemplated herein if the barrier layer (BS) is arranged on the side coming into contact with the bleaching agent composition. The first polymer layer (P1) thus on the one hand borders the barrier layer (BS) and on the other hand the second polymer layer (P2), which is disposed on the outer side of the package. The polymer layer (P1) is different here from the polymer layer (P2). Here, the barrier layer (BS) serves as a carrier layer, to which the first polymer layer (P1) is then applied. The second polymer layer (P2) is then applied to the aforementioned polymer layer (P1). The three layers (BS), (P1) and (P2) together form a film (F), the total thickness of which is preferably from about 30 μm to about 1.0 mm.

Within the scope of the present disclosure, however, an arrangement in which the barrier layer (BS) lies between the first polymer layer (P1) and the second polymer layer (P2) is particularly preferred. In this case the multi-layer film (F) includes three layers, wherein the layer (P1) is innermost and is in contact with the bleaching agent composition. The layer (P1) is in contact with the barrier layer (BS), and the barrier layer (BS) in turn is in contact with the layer (P2). With this layered arrangement the layers (P1) and (P2) are not adjacent to one another, but are separated by the barrier layer (BS). With this arrangement the layers (P1) and (P2) can include in principle the same polymer material, however it is preferred if the two layers (P1) and (P2) include different polymer materials. The three layers (P1), (BS) and (P2) together form a film (F), the total thickness of which is preferably from about 30 μm to about 1.0 mm. The particular advantage of this arrangement lies in the fact that the—often very thin—barrier layer (BS) is disposed neither on the inner nor on the outer surface of the multi-layer film (F), but instead is protected in the direction of the inner side by the polymer layer (P1) and in the direction of the outer side by the polymer layer (P2). With this arrangement, mechanical abrasion or mechanical destruction of the barrier layer (BS) can thus be avoided to the best possible extent. It is therefore advantageous within the scope of the present disclosure if the at least one multi-layer film (F) contains the at least one barrier layer (BS) between the at least one first polymer layer (P1) and the at least one second polymer layer (P2). The use of packages of this kind has proven to be particularly advantageous in respect of the increased storage stability, since this arrangement demonstrates no expansion or delamination in the event of relatively long periods of contact with an oxidizing agent-containing composition.

Likewise particularly preferred as contemplated herein is a film (F) in which the first polymer layer (P1) is arranged on the side coming into contact with the bleaching agent composition. The second polymer layer (P2) borders the polymer layer (P1) and is different therefrom. The barrier layer (BS) is disposed externally. In films (F) having this layer arrangement, the layer (P1) for example can function as a polymer carrier layer, to which the second polymer layer (P2) is then applied. The side bordering (P2) (i.e. the outer side) is then provided with the barrier layer. It is therefore advantageous within the scope of the present disclosure if the at least one multi-layer film (F) contains the at least one barrier layer (BS) on the outer side of the package (VP). As contemplated herein the outer side of the package (VP) is understood to mean the side of the package that does not come into contact with the bleaching agent composition, but instead is in contact with the surrounding environment. The three layers (P1), (P2) and (BS) together form a film (F), the total thickness of which is preferably from about 30 μm to about 1.0 mm. The use of packages of this kind has proven to be particularly advantageous in respect of the increased storage stability, since this arrangement demonstrates no expansion or delamination in the event of relatively long periods of contact with an oxidizing agent-containing composition.

If the multi-layer film (F) contains the previously described three layers (P1), (P2) and (BS), suitable arrangements of the layers as contemplated herein are described hereinafter (as considered from the interior (in contact with the bleaching agent composition) towards the outer side):
a) *interior*-layer (P1)-layer (P2)-barrier layer (BS)-*outer side*,
b) *interior*-layer (P1)-barrier layer (BS)-layer (P2)-*outer side*,
c) *interior*-layer (P2)-layer (P1)-barrier layer (BS)-*outer side*,
d) *interior*-layer (P2)-barrier layer (BS)-layer (P1)-*outer side*,
e) *interior*-barrier layer (BS)-layer (P1)-layer (P2)-*outer side*,
f) *interior*-barrier layer (BS)-layer (P2)-layer (P1)-*outer side*, The first polymer material of the first layer (P1) is an organic polymer material as contemplated herein. This feature may be a layer formed of a polymer type or a layer formed of a polymer blend. This first layer (P1) may function for example as a polymer carrier material, i.e. during the production of the film a layer or a film made of the polymer material (P1) may be presented and then sprayed, laminated or coated with the further layers as contemplated herein. Preferred embodiments of the present disclosure are exemplified in that the at least one first polymer layer (P1) is formed from polypropylene, polyethylene, polyester, polyamide or polyvinyl alcohol, in particular from polypropylene. The term "is formed" is understood as contemplated herein to mean that the polymer layer contains at least about 70 wt %, preferably at least about 80 wt %, preferably at least about 90 wt %, in particular at least about 99 wt %, in each case in relation to the total weight of the polymer layer (P1), of the previously described compounds.

A particularly preferred product as contemplated herein is therefore exemplified in that the multi-layer film (F) comprises at least one first polymer layer (P1) which is formed from polypropylene. Polypropylene is alternatively also referred to as poly(1-methylethylene) and is a thermoplastic polymer belonging to the group of polyolefins. Polypropylene is produced by polymerisation of propylene (propene) with use of various catalysts. Polypropylene for example can thus be produced by stereospecific polymerisation of propylene in the gas phase or in suspension as described by Giulio Natta. Polypropylenes as contemplated herein can be isotactic and thus highly crystalline, or syndiotactic or amorphous. The mean relative molar mass can be controlled for example by setting a certain hydrogen partial pressure during the polymerisation of the propene. For example, polypropylene can have mean relative molar masses of approximately 150,000 to about 1,500,000 g/mol. Polypropylene can be processed for example by extrusion and stretch blow moulding methods, or by pressing, calendering, thermoforming and cold-forming.

The first polymer layer (P1) preferably has a certain layer thickness. It is therefore preferred within the scope of the present disclosure if the at least one first polymer layer (P1) has a layer thickness of from about 20.0 μm to about 300 μm, preferably from about 40.0 μm to about 200 μm, preferably from about 50.0 μm to about 100 μm, in particular from about 60.0 μm to about 90.0 μm.

A particularly preferred product as contemplated herein is therefore exemplified in that the multi-layer film (F) comprises at least one first polymer layer (P1) which is formed from polypropylene and has a layer thickness of from about 60.0 to about 90.0 μm.

Furthermore, the multi-layer film (F) from which the package is produced comprises a second polymer layer (P2) made of a second polymer material. The second polymer material may be a layer formed of one polymer type or a layer formed of a polymer blend. When producing the multi-layer film, the second layer (P2) for example—either before or after application of the barrier layer (BS) to the first polymer layer (P1) functioning as carrier layer, can be sprayed on, spread on or stratified. However, it is also conceivable that the second polymer layer (P2) functions as carrier layer, to which the barrier layer (BS) and the first polymer layer (P1) are then applied.

Depending on the previously described sequence of the coating, the first polymer material of the first polymer layer (P1) and the second polymer material of the second polymer layer (P2) can be either the same (if the two layers are not in contact with one another) or also different. The polymer layer (P2) can therefore be formed from the compounds mentioned previously in conjunction with the polymer layer (P1). The layers (P1) and (P2) are preferably produced from different polymer materials (i.e. different polymers or polymer blends). It is therefore preferred within the scope of the present disclosure if the at least one second polymer layer (P2) is formed from polyethylene terephthalate or polyethylene naphthalate, in particular from polyethylene terephthalate. The term "is formed" is understood as contemplated herein to mean that the polymer layer contains at least about 70 wt %, preferably at least about 80 wt %, preferably at least about 90 wt %, in particular at least about 99 wt %, in each case in relation to the total weight of the polymer layer (P2), of the previously described compounds. Polyethylene terephthalate (PET) is a polymer from the group of polyesters. Polyethylene terephthalate can be produced for example by transesterification of dimethyl terephthalate with ethylene glycol at higher temperatures. In this transesterification reaction, methanol is cleaved off and is removed by distillation. The resultant bis(2-hydroxyethyl)terephthalate is reacted by polycondensation to form PET, wherein ethylene glycol is created in turn. A further method for producing polyethylene terephthalate is direct polycondensation of ethylene glycol and terephthalic acid at high temperatures with the resultant water being distilled off The second polymer layer (P2) preferably has a smaller layer thickness than the polymer layer (P1). It is therefore advantageous within the scope of the present disclosure if the at least one second polymer layer (P2) has a layer thickness of from about 1.00 μm to about 100 μm, preferably from about 2.50 μm to about 50.0 μm, preferably from about 5.00 μm to about 25.0 μm, in particular from about 10.0 μm to about 20.0 μm.

A particularly preferred product as contemplated herein is therefore exemplified in that the multi-layer film (F) comprises at least one second polymer layer (P2) which is formed from polyethylene terephthalate and has a layer thickness of from about 10.0 to about 20.0 μm.

The polymer layers (P1) and (P2) of the multi-layer film (F) include organic polymer materials which generally have only an insufficient barrier effect with respect to gases and water vapour. If the oxidizing agent-containing composition is packaged in a package (VP) formed from a multi-layer film (F) which comprises merely the two organic polymer layers (P1) and (P2), water vapour can escape unhindered, and therefore the water content in the composition changes unacceptably when said composition is stored over a relatively long period. In order to selectively minimise the uncontrolled escape of water vapour from the package (VP), the organic polymer layers (P1) and (P2) are therefore used in combination with a barrier layer (BS).

The barrier layer (BS) has a penetration barrier effect for gases and water vapour. What is meant by this as contemplated herein is that the barrier layer (BS) reduces the rate of permeation of water vapour and of gases through the film. A film (F) as contemplated herein which also has a barrier layer (BS) in addition to the layers (P1) and (P2) thus has a reduced water vapour permeability and a reduced gas permeability compared to a comparable film (of equal total thickness) which comprises merely the two layers (P1) and (P2), but no barrier layer (BS).

The barrier layer (BS) for example is a thin layer which comprises inorganic material, wherein the inorganic material can be applied to the organic polymer layer (P1) and/or (P2) with the aid of vacuum coating techniques (for example PVD or physical vapour deposition, or CVD or chemical vapour deposition).

The barrier layer (BS) is a layer which comprises at least one inorganic material, for example aluminium, aluminium oxides, magnesium, magnesium oxides, silicon, silicon oxides, titanium, titanium oxides, tin, tin oxides, zirconium, zirconium oxide and/or carbon can be considered here. In this regard, oxides are particularly preferably used and can be selected from the group of aluminium oxides, magnesium oxides, silicon oxides, titanium oxides, tin oxides and/or zirconium oxides. Within the scope of the present disclosure the barrier layer (BS) is formed by an aluminium layer.

The barrier layer (BS) formed from inorganic material is located very particularly preferably between the two polymer layers (P1) and (P2). The production of films with barrier layers formed from inorganic material is described for example in document EP 1036813 A1, the entire content of which is referred to at this juncture.

The thicker the barrier layer (BS), the greater or stronger is the penetration barrier effect for gases and water vapour. The thickness of the barrier layer (BS) may therefore be selected depending on the desired barrier layer effect. The barrier layer (BS) for example may have a layer thickness of from about 1 to about 1000 nm (nanometres). The barrier layer (BS) preferably has a layer thickness of from about 5 to about 500 nm, more preferably of from about 10 to about 250 nm, and particularly preferably from about 10 to about 150 nm (nanometres). Preferred embodiments of the present disclosure are therefore exemplified in that the at least one barrier layer (BS) has a layer thickness of from about 1.00 nm to about 1,000 nm, preferably from about 5.00 nm to about 500 nm, preferably from about 10.0 nm to about 250 nm, in particular from about 10.0 nm to about 150 nm.

Besides the previously described layers (P1), (P2) and (BS), the multi-layer film (F) may additionally also comprise one or more further layers. These further layers can be intermediate layers and/or adhesive layers, for example. It is therefore preferred as contemplated herein if the at least one multi-layer film (F) additionally contains at least one further layer, selected from the group of intermediate layers (SZ), adhesive layers (SK) and mixtures thereof.

For example, the films (F) can have further intermediate layers (SZ) in order to increase the mechanical stability. Intermediate layers can also prevent or minimise the permeation of polymers or remaining monomers from a polymer layer into the bleaching agent composition.

In order to increase the bond strength, the films can additionally also comprise one or more adhesive layers (SK) so as to reduce or to prevent a delamination (i.e. a detachment or the formation of an air pocket) between two layers.

A particularly preferred product as contemplated herein is exemplified in that the multi-layer film (F), besides the first polymer layer (P1), the second polymer layer (P2) and the barrier layer (BS), additionally also contains one or more further layers which are selected from intermediate layers (SZ) and/or adhesive layers (SK).

If the multi-layer film (F), in addition to the layers (P1), (P2) and (BS), also contains further layers, suitable arrangements as contemplated herein of the layers are described hereinafter (as considered from the interior (in contact with the bleaching agent composition) to the outer side):

a) *interior*-layer (P1)-first adhesive layer (SK1)-layer (P2)-second adhesive layer (SK2)-barrier layer (BS)-*outer side*,
b) *interior*-layer (P1)-adhesive layer (SK1)-layer (P2)-barrier layer (BS)-*outer side*,
c) *interior*-layer (P1)-layer (P2)-second adhesive layer (SK2)-barrier layer (BS)-*outer side*,
d) *interior*-barrier layer (BS)-first adhesive layer (SK1)-layer (P1)-second adhesive layer (SK2)-layer (P2)-*outer side*,
e) *interior*-barrier layer (BS)-adhesive layer (SK)-layer (P1)-layer (P2)-*outer side*,
f) *interior*-barrier layer (BS)-layer (S1)-adhesive layer (SK)-layer (P2)-*outer side*,
g) *interior*-layer (P1)-first adhesive layer (SK1)-barrier layer (BS)-second adhesive layer (SK2)-layer (P2)-*outer side*,
h) *interior*-layer (P1)-adhesive layer (SK)-barrier layer (BS)-layer (P2)-*outer side*,
i) *interior*-layer (P1)-barrier layer (BS)-adhesive layer (SK)-layer (P2)-*outer side*, The object forming the basis of the present disclosure is also achieved by the subject matter of claim 10. A second subject of the present disclosure is therefore a method for bleaching human hair, in which (a) the cosmetic product according to the first subject of the present disclosure is introduced into an amount of water, (b) the obtained mixture from (a) is homogenised, and (c) the homogenised mixture from (b) is applied to the human hair.

As already described above, the advantage of the present disclosure lies in the fact that an individual packaged item is provided, the content of which is added to water so that the bleaching agent composition is suspended and the homogenised mixture then forms a ready-to-use bleaching composition. After application, the homogenised mixture is then left to take effect and lastly is washed out from the hair using water. Bleached hair is produced in this way.

In accordance with a preferred embodiment of the present disclosure, the mixing ratio of bleaching agent composition to water may be in the range from about 1:5 (about 1 part by weight of agent as contemplated herein to about 3 parts by weight of water) to about 3:1, preferably from about 1:2 to about 1:1.

The ready-to-use cosmetic product prepared from the cosmetic product and water preferably have a viscosity in the range from about 3000 to about 40000 mPas, preferably from about 4000 to about 30000 mPas, particularly preferably from about 6000 to about 15000 mPas, measured in each case at 20° C. with a Haake-cylinder/cylinder viscometer, SV I rotary/measurement system with a cooling time of 5 minutes. With this measurement method, the viscosity value is determined for a shear rate of 1/7.2 s. The measurement program works with a ramp of 0-1/60 s. A viscosity in this range enables the ready-to-use cosmetic product to be applied well, and also lends it a flow behaviour such that the application site is exposed to the product for long enough to guarantee that it will have the intended effect on the keratinous fibres.

The exposure time after step c) described above is preferably from about 5 to about 60 min, particularly from about 5 to about 50 min, particularly preferably from about 10 to about 45 min. During the exposure time for the homogenised mixture on the hair, it may be advantageous to support the dyeing process by adding heat. The exposure phase at room temperature also falls within the scope of the present disclosure. In particular, the temperature during the exposure time is between about 20° C. and about 40° C., particularly between about 25° C. and about 38° C. The products already deliver good treatment results at physiologically tolerable temperatures of below about 45° C.

After the end of the exposure phase, all components remaining on the keratin fibres are rinsed out of the hair with water or a surfactant-containing cleaning agent. In this context, cleaning agents may particularly be standard commercial shampoo, wherein the cleaning agent may particularly be omitted and the rinsing process may be carried out with tap water if the dyeing agent has a higher surfactant content.

Features relating to preferred embodiments of the first object of the present disclosure which are only described with reference thereto in the preceding text are naturally also applicable correspondingly as features of preferred embodiments for the second and third objects.

The examples hereinafter are intended to explain the subject matter of the present disclosure without limiting it in any way.

EXAMPLES

Formulations

The following formulations were produced (unless stated otherwise, the quantity specifications are in wt %)

Bleaching Powder

|  | KM 1 | KM 2 |
| --- | --- | --- |
| Britesil C 265 | 22.4 | 27.0 |
| Magnesium carbonate (heavy) | 30.8 | 2.6 |
| Carboxymethyl cellulose (Cekol 50000) | 1.9 | 2.2 |
| Hydroxyethyl cellulose (Tylose H 100000 YP 2) | 1.9 | 2.3 |
| Xanthan Gum (Keltrol CG-SFT) | 2.4 | 3.7 |
| EDETA BX Powder | 1.6 | 1.6 |
| NaCl | 0.5 | 0.5 |
| Citric acid | 0.5 |  |
| L-Arginine | 1.0 |  |
| Ammonium persulfate + 0.5% silica | 10.0 | 14.0 |
| Potassium persulfate | 19.0 | 27.4 |
| Sodium persulfate | 5.0 | 6.0 |
| Dimethicone/Dimethiconol | 3.0 | 2.4 |
| Sodium percarbonate | — | 10.0 |

The composition KM 1 was produced as a two-chamber sachet, wherein 23 g of KM 1 were filled into the first chamber and 2 g of percarbonate were filled into the second chamber.

The mixing ratio of the cosmetic product and water was 1:2 in the case of the two-chamber sachet, wherein 50 g of water were used, and 1:3 in the case of the single-chamber sachet, wherein 75 g of water were used.

The following compositions were also produced:

Bleaching Powder

|  | KM 3 | KM 4 | KM 5 |
| --- | --- | --- | --- |
| Magnesium carbonate (heavy) | 12 | 22.8 | 2.6 |
| Britesil C 265 | 36.5 | 22.4 | 27 |
| Carboxymethyl cellulose (Cekol 50000) | 2 | 1.9 | 2.2 |
| Hydroxyethyl cellulose (Tylose H 100000 YP 2) | 2 | 1.9 | 2.3 |
| Xanthan Gum (Keltrol CG-SFT) | 3.5 | 2.4 | 3.7 |
| EDETA BX Powder | 1.5 | 1.6 | 1.6 |
| Sodium persulfate | 5 | 5 | 6 |
| Ammonium persulfate + 0.5% silica | 14.5 | 10 | 14 |
| Potassium persulfate | 14.5 | 19 | 27.4 |
| Eumulgin B5 | 4.5 |  |  |
| NaCl | 0.5 | 0.5 | 0.5 |
| Dimethicone/Dimethiconol | 3 | 3 | 2.4 |
| Citric acid | 0.5 | 0.5 |  |
| L-Arginine |  | 1 |  |
| Sodium percarbonate | 8 | 8 | 10 |
| Perfume |  |  | 0.3 |

Application

The preparations comprising KM 1 and KM 2 were provided for the application.

The bag contents were blended with lukewarm water and homogenised. The homogenised mixtures were applied to light-brown Fischbach & Miller hair and left to take effect for 45 minutes, and were then washed out using tap water. The hair was then dried.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic product for bleaching keratin fibres, comprising:
   (i) a package comprising at least one multi-layer film, which comprises at least one metal-containing layer as a barrier layer; and
   (ii) a bleaching agent composition, which is contained in the package; wherein
   the bleaching agent composition comprises
      at least one percarbonate,
      at least one inorganic salt of a peroxysulfuric acid, and
      at least one thickener.

2. The cosmetic product according to claim 1, wherein the at least one inorganic salt of a peroxysulfuric acid is selected from the group of sodium peroxydisulfate, potassium peroxydisulfate, ammonium peroxydisulfate, sodium peroxymonosulfate, potassium peroxymonosulfate and ammonium peroxymonosulfate, and mixtures of these inorganic salts of a peroxysulfuric acid, and wherein the total quantity of inorganic salt of a peroxy sulfuric acid is from about 10 to about 70 wt %, in relation to a total weight of the bleaching agent composition.

3. The cosmetic product according to claim 1, wherein the inorganic salt of a peroxy sulfuric acid is a mixture comprising from about 5 to about 40 wt % potassium peroxydisulfate, from about 5 to about 20 wt % ammonium peroxydisulfate, and from about 0 to about 10 wt % sodium peroxydisulfate, in each case in relation to a total weight of the bleaching agent composition.

4. The cosmetic product according to claim 1, wherein the at least one percarbonate is an alkaline, alkaline earth metal or ammonium salt of a percarbonate, and wherein the bleaching agent composition comprises the at least one percarbonate in a total quantity of from about 2 to about 14 wt % in relation to a total weight of the bleaching agent composition.

5. The cosmetic product according to claim 1, wherein the at least one thickener comprises a polysaccharide, wherein the bleaching agent composition comprises the at least one thickener in a total quantity of from about 0.5 to about 15 wt %, in relation to a total weight of the bleaching agent composition.

6. The cosmetic product according to claim 1, wherein the at least one thickener is a mixture of a cellulose gum, a hydroxyethyl cellulose and a xanthan gum, wherein the quantity of cellulose gum is from about 0.2 to about 5 wt %, the quantity of xanthan gum is from 0.1 to 5 wt %, and the quantity of hydroxyethyl cellulose is from 0.2 to 5 wt %, in each case in relation to a total weight of bleaching agent composition.

7. The cosmetic product according to claim 1, wherein the multi-layer film comprises at least one first polymer layer (P1), at least one second polymer layer (P2) and the barrier layer (BS), wherein the first polymer layer (P1) is formed from polyethylene terephthalate or polyethylene naphthalate; the second polymer layer (P2) is formed from a polyolefin; and the barrier layer (BS) comprises aluminium; wherein the first polymer layer (P1) has a layer thickness of from about 5 to about 20 µm, the second polymer layer has a layer thickness of from about 50 to about 100 µm, and the barrier layer has a layer thickness of from 3 to 30 µm.

8. The cosmetic product according to claim 7, wherein the barrier layer (BS) is arranged between the first polymer layer (P1) and the second polymer layer (P2), and wherein the first polymer layer is situated on the side facing away from the bleaching agent composition.

9. The cosmetic product according to claim 1, wherein the package is a one-chamber sachet in which the percarbonate and the inorganic salt of a peroxysulfuric acid are present;
   wherein the multi-layer film (F) has an oxygen transmission rate (OTR) of less than about 0.1 cc/m2/d/bar at 23° C. and 0% relative humidity, and a water vapour permeability of less than about 0.1 g/m2d at 38° C. and 90% relative humidity.

10. A method for bleaching human hair, the method comprising the steps of:
   (a) introducing the bleaching agent composition according to claim 1 into an amount of water,
   (b) homogenizing the obtained mixture from (a), and
   (c) applying the homogenised mixture from (b) to the human hair.

11. The cosmetic product according to claim 1, wherein:
   the package is a two-chamber bag and the percarbonate is contained in a first chamber of the two-chamber bag and the inorganic salt of a peroxysulfuric acid is contained in a second chamber of the two-chamber bag; and
   wherein the multi-layer film (F) has an oxygen transmission rate (OTR) of less than about 0.1 cc/m2/d/bar at 23° C. and 0% relative humidity, and a water vapour permeability of less than about 0.1 g/m2d at 38° C. and 90% relative humidity.

12. The cosmetic product according to claim 1 wherein:
   the at least one inorganic salt of a peroxysulfuric acid is selected from the group of mixtures of potassium peroxydisulfate and ammonium peroxydisulfate, and mixtures of sodium peroxydisulfate and ammonium peroxydisulfate; and
   wherein the total quantity of inorganic salt of a peroxysulfuric acid is from about 10 to about 70 wt %, in relation to a total weight of the bleaching agent composition.

13. The cosmetic product according to claim 7, wherein:
   the first polymer layer (P1) has the layer thickness of from about 8 to about 16 µm, the second polymer layer (P2) has the layer thickness of from about 60 to about 90 µm, and the barrier layer (BS) has the layer thickness of from about 5 to about 15 µm.

14. The cosmetic product according to claim 7, wherein:
   the first polymer layer (P1) has the layer thickness of from about 10 to about 14 µm, the second polymer layer (P2) has the layer thickness of from about 70 to about 80 µm, and the barrier layer (BS) has the layer thickness of from about 8 to about 12 µm.

15. The cosmetic product according to claim 1, wherein:
   wherein the at least one thickener comprises a mixture of an at least partially ionic polysaccharide and a non-ionic polysaccharide, wherein the bleaching agent composition comprises the at least one thickener in a total quantity of from about 0.5 to about 15 wt %, in relation to a total weight of the bleaching agent composition.

16. The cosmetic product according to claim 15, wherein:
   the bleaching agent composition comprise the at least one thickener in a total quantity of from about 4 to about 8 wt %, in relation to the total weight of the bleaching agent composition.

17. The cosmetic product according to claim 7, wherein: the first polymer layer (P1) comprises polyethylene terephthalate, and the second polymer layer (P2) comprises polyethylene.

18. The cosmetic product according to claim 1, wherein; the at least one percarbonate is sodium percarbonate, and wherein the bleaching agent composition comprises the sodium percarbonate in a total quantity of from about 6 to about 12 wt %, in relation to a total weight of the bleaching agent composition.

19. A cosmetic product comprising:
(i) a package comprising at least one multi-layer film, wherein the multi-layer film comprises a first polymer layer (P1), a second polymer layer (P2) and a barrier layer (BS), wherein the first polymer layer (P1) comprises polyethylene terephthalate and has a layer thickness of from about 10 to about 14 μm, the second polymer layer (P2) comprises polyethylene and has a layer thickness of from about 70 to about 80 μm, and the barrier layer (BS) comprises aluminium and has a layer thickness of from about 8 to about 12 μm; and
(ii) a bleaching agent composition, which is contained in the package; wherein the bleaching agent composition comprises
a percarbonate that is sodium percarbonate, wherein the sodium percarbonate is present in the bleaching agent composition at from about 6 to about 12 wt %,
an inorganic salt of a peroxysulfuric acid, wherein the at least one inorganic salt of a peroxysulfuric acid is selected from the group of mixtures of potassium peroxydisulfate and ammonium peroxydisulfate, and mixtures of sodium peroxydisulfate and ammonium peroxydisulfate, and the at least one inorganic salt of a peroxysulfuric acid is present in the bleaching agent composition at from about 10 to about 70 wt %; and
a thickener, wherein the at least one thickener comprises a mixture of a cellulose gum, a hydroxyethyl cellulose and a xanthan gum, wherein the quantity of cellulose gum is from about 0.2 to about 5 wt %, the quantity of xanthan gum is from 0.1 to 5 wt %, and the quantity of hydroxyethyl cellulose is from 0.2 to 5 wt %, wherein all wt % values are in relation to a total weight of the bleaching agent composition.

\* \* \* \* \*